(12) United States Patent
Schaller

(10) Patent No.: US 9,987,163 B2
(45) Date of Patent: Jun. 5, 2018

(54) DEVICE FOR DISPENSING INTRAOCULAR SUBSTANCES

(71) Applicant: Novartis AG, Basel (CH)

(72) Inventor: Michael Schaller, Menlo Park, CA (US)

(73) Assignee: Novartis AG, Basel (CH)

( * ) Notice: Subject to any disclaimer, the term of this patent is extended or adjusted under 35 U.S.C. 154(b) by 887 days.

(21) Appl. No.: 14/254,366

(22) Filed: Apr. 16, 2014

(65) Prior Publication Data

US 2014/0309599 A1    Oct. 16, 2014

Related U.S. Application Data

(60) Provisional application No. 61/812,606, filed on Apr. 16, 2013.

(51) Int. Cl.
| *A61F 9/00* | (2006.01) |
| *A61M 5/315* | (2006.01) |
| *A61M 5/24* | (2006.01) |
| *A61M 5/31* | (2006.01) |

(52) U.S. Cl.
CPC ....... *A61F 9/0008* (2013.01); *A61M 5/31526* (2013.01); *A61F 9/0017* (2013.01); *A61M 2005/2407* (2013.01); *A61M 2005/3143* (2013.01)

(58) Field of Classification Search
CPC ....................................................... A61F 9/00
See application file for complete search history.

(56) References Cited

U.S. PATENT DOCUMENTS

| 3,439,675 A | 4/1969 | Cohen |
| 3,767,759 A | 10/1973 | Wichterle |
| 3,788,327 A | 1/1974 | Donowitz et al. |
| 3,915,172 A | 10/1975 | Wichterle et al. |
| 4,037,604 A | 7/1977 | Newkirk |
| 4,402,681 A | 9/1983 | Haas et al. |
| 4,457,757 A | 7/1984 | Molteno |
| 4,521,210 A | 6/1985 | Wong |

(Continued)

FOREIGN PATENT DOCUMENTS

| CN | 1285724 A | 2/2001 |
| EP | 0 228 185 A1 | 11/1986 |

(Continued)

OTHER PUBLICATIONS

Barsky et al. "Evaluation of absorbable gelatin film (Gelfilm) in cyclodialysis clefts" Arch. Ophth. 60(6): 1044-1052, 1958.

(Continued)

*Primary Examiner* — Todd J Scherbel
*Assistant Examiner* — Sara Sass
(74) *Attorney, Agent, or Firm* — Mintz Levin Cohn Ferris Glovsky and Popeo, P.C.

(57) ABSTRACT

This disclosure relates generally to an injection device having a plunger configured to advance a distance into a container of material, such as a viscoelastic container; a trigger mechanism configured upon an actuation of the trigger mechanism to apply a first force to a spring element; and the spring element coupled to the plunger and configured to apply a second force to the plunger and which is configured to prevent exceeding a threshold maximum force applied to the container.

26 Claims, 11 Drawing Sheets

(56) References Cited

U.S. PATENT DOCUMENTS

| | | |
|---|---|---|
| 4,554,918 A | 11/1985 | White |
| 4,604,087 A | 8/1986 | Joseph |
| 4,634,418 A | 1/1987 | Binder |
| 4,722,724 A | 2/1988 | Schocket |
| 4,750,901 A | 6/1988 | Molteno |
| 4,787,885 A | 11/1988 | Binder |
| 4,826,478 A | 5/1989 | Schocket |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,284,476 A | 2/1994 | Koch |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,423,777 A | 6/1995 | Tajiri et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,558,629 A | 9/1996 | Baerveldt et al. |
| 5,558,630 A | 9/1996 | Fisher |
| 5,571,189 A * | 11/1996 | Kuslich ............... A61B 17/7098 623/17.12 |
| RE35,390 E | 12/1996 | Smith |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,749,879 A | 5/1998 | Middleman et al. |
| 5,752,928 A | 5/1998 | de Roulhac et al. |
| 5,807,244 A | 9/1998 | Barot |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,941,250 A | 8/1999 | Aramant et al. |
| 5,968,058 A | 10/1999 | Richter et al. |
| 6,007,510 A | 12/1999 | Nigam |
| 6,007,511 A | 12/1999 | Prywes |
| 6,019,786 A | 2/2000 | Thompson |
| 6,036,678 A | 3/2000 | Giungo |
| 6,050,970 A | 4/2000 | Baerveldt |
| 6,050,999 A | 4/2000 | Paraschac et al. |
| 6,077,299 A | 6/2000 | Adelberg et al. |
| 6,102,045 A | 8/2000 | Nordquist et al. |
| 6,142,969 A | 11/2000 | Nigam |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,331,313 B1 | 12/2001 | Wong et al. |
| 6,375,642 B1 | 4/2002 | Grieshaber et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,494,857 B1 | 12/2002 | Neuhann |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,561,974 B1 | 5/2003 | Grieshaber et al. |
| 6,579,256 B2 | 6/2003 | Hughes |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,726,676 B2 | 4/2004 | Stegmann et al. |
| 6,730,056 B1 | 5/2004 | Ghaem et al. |
| 6,736,791 B1 | 5/2004 | Tu et al. |
| 6,741,666 B1 | 5/2004 | Henry et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,710 B2 | 10/2008 | Tu et al. |
| 7,488,303 B1 | 2/2009 | Haffner et al. |
| RE40,722 E | 6/2009 | Chappa |
| 7,563,241 B2 | 7/2009 | Tu et al. |
| 7,708,711 B2 | 5/2010 | Tu et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 8,075,511 B2 | 12/2011 | Tu et al. |
| 8,172,899 B2 | 5/2012 | Silvestrini et al. |
| 8,721,656 B2 | 5/2014 | De Juan, Jr. et al. |
| 2001/0000527 A1 | 4/2001 | Yaron et al. |
| 2001/0025150 A1 | 9/2001 | de Juan et al. |
| 2002/0013546 A1 | 1/2002 | Grieshaber et al. |
| 2002/0013572 A1 | 1/2002 | Berlin |
| 2002/0026200 A1 | 2/2002 | Savage |
| 2002/0072673 A1 | 6/2002 | Yamamoto et al. |
| 2002/0087111 A1 | 7/2002 | Ethier et al. |

(56) References Cited

U.S. PATENT DOCUMENTS

| | | |
|---|---|---|
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0156413 A1 | 10/2002 | Williams et al. |
| 2002/0165478 A1 | 11/2002 | Gharib et al. |
| 2002/0169130 A1 | 11/2002 | Tu et al. |
| 2002/0169468 A1 | 11/2002 | Brown |
| 2002/0177856 A1 | 11/2002 | Richter et al. |
| 2002/0188308 A1 | 12/2002 | Tu et al. |
| 2002/0193725 A1 | 12/2002 | Odrich |
| 2003/0009124 A1 | 1/2003 | Lynch et al. |
| 2003/0028228 A1 | 2/2003 | Sand |
| 2003/0055372 A1 | 3/2003 | Lynch et al. |
| 2003/0060752 A1 | 3/2003 | Bergheim et al. |
| 2003/0069637 A1 | 4/2003 | Lynch et al. |
| 2003/0088260 A1 | 5/2003 | Smedley et al. |
| 2003/0097151 A1 | 5/2003 | Smedley et al. |
| 2003/0097171 A1 | 5/2003 | Elliott |
| 2003/0120200 A1 | 6/2003 | Bergheim et al. |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0187385 A1 | 10/2003 | Bergheim et al. |
| 2003/0191428 A1 | 10/2003 | Bergheim et al. |
| 2003/0208163 A1 | 11/2003 | Yaron et al. |
| 2003/0220602 A1 | 11/2003 | Lynch et al. |
| 2003/0220603 A1 | 11/2003 | Lynch et al. |
| 2003/0229303 A1 | 12/2003 | Haffner et al. |
| 2003/0232015 A1 | 12/2003 | Brown et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0050392 A1 | 3/2004 | Tu et al. |
| 2004/0073156 A1 | 4/2004 | Brown |
| 2004/0088048 A1 | 5/2004 | Richter et al. |
| 2004/0092856 A1 | 5/2004 | Dahan |
| 2004/0097984 A1 | 5/2004 | Zapata |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0148022 A1 | 7/2004 | Eggleston |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260227 A1 | 12/2004 | Lisk et al. |
| 2004/0260228 A1 | 12/2004 | Lynch et al. |
| 2005/0008673 A1 | 1/2005 | Snyder et al. |
| 2005/0038334 A1 | 2/2005 | Lynch et al. |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0171507 A1 | 8/2005 | Christian et al. |
| 2005/0175663 A1 | 8/2005 | Hunter et al. |
| 2005/0181011 A1 | 8/2005 | Hunter et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0232972 A1 | 10/2005 | Odrich |
| 2005/0244462 A1 | 11/2005 | Farooq |
| 2005/0245911 A1 | 11/2005 | Wright et al. |
| 2005/0250788 A1 | 11/2005 | Tu et al. |
| 2005/0266047 A1 | 12/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0288617 A1 | 12/2005 | Yaron et al. |
| 2005/0288619 A1 | 12/2005 | Gharib et al. |
| 2006/0004348 A1 | 1/2006 | Scheller et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0047263 A1 | 3/2006 | Tu et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0149194 A1 | 7/2006 | Conston et al. |
| 2006/0155238 A1 | 7/2006 | Shields |
| 2006/0155300 A1 | 7/2006 | Stamper et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2006/0276739 A1 | 12/2006 | Brown |
| 2007/0010827 A1 | 1/2007 | Tu et al. |
| 2007/0088242 A1 | 4/2007 | Coroneo |
| 2007/0088424 A1 | 4/2007 | Greenberg et al. |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0149915 A1 | 6/2007 | Yablonski |
| 2007/0191863 A1 | 8/2007 | De Juan et al. |
| 2007/0207186 A1 | 9/2007 | Scanlon et al. |
| 2007/0233037 A1 | 10/2007 | Gifford et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0027304 A1* | 1/2008 | Pardo ............... A61F 2/16 600/399 |
| 2008/0045878 A1 | 2/2008 | Bergheim et al. |
| 2008/0058704 A1 | 3/2008 | Hee et al. |
| 2008/0108933 A1* | 5/2008 | Yu ............... A61M 27/008 604/8 |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0043321 A1 | 2/2009 | Conston et al. |
| 2009/0138022 A1 | 5/2009 | Tu et al. |
| 2009/0182421 A1 | 7/2009 | Silvestrini et al. |
| 2010/0010416 A1 | 1/2010 | Juan, Jr. et al. |
| 2010/0134759 A1 | 6/2010 | Silvestrini et al. |
| 2010/0137981 A1 | 6/2010 | Silvestrini et al. |
| 2010/0152641 A1 | 6/2010 | Yablonski |
| 2010/0268232 A1* | 10/2010 | Betz ............... A61F 2/30 606/79 |
| 2010/0274259 A1 | 10/2010 | Yaron et al. |
| 2011/0028883 A1 | 2/2011 | Juan, Jr. et al. |

(56) References Cited

U.S. PATENT DOCUMENTS

| | | |
|---|---|---|
| 2011/0028884 A1 | 2/2011 | Theodore Coroneo |
| 2011/0087149 A1 | 4/2011 | Theodore Coroneo |
| 2011/0087150 A1 | 4/2011 | Theodore Coroneo |
| 2011/0087151 A1 | 4/2011 | Theodore Coroneo |
| 2011/0098629 A1 | 4/2011 | Juan, Jr. et al. |
| 2011/0306915 A1 | 12/2011 | De Juan, Jr. et al. |

FOREIGN PATENT DOCUMENTS

| | | |
|---|---|---|
| EP | 1173124 B1 | 1/2002 |
| EP | 1173125 B1 | 1/2002 |
| EP | 1173126 B1 | 1/2002 |
| EP | 1184010 A2 | 3/2002 |
| EP | 1278492 B1 | 1/2003 |
| EP | 1292256 A1 | 3/2003 |
| EP | 1310222 A2 | 5/2003 |
| EP | 1473004 A2 | 11/2004 |
| EP | 1477146 A2 | 11/2004 |
| EP | 1651291 B1 | 5/2006 |
| EP | 1418868 B1 | 3/2008 |
| EP | 1977724 A1 | 10/2008 |
| EP | 1545655 B1 | 12/2008 |
| EP | 2027837 A2 | 2/2009 |
| GB | 2101891 A | 1/1983 |
| JP | 2007-535386 A | 12/2007 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | WO-89/00869 A1 | 2/1989 |
| WO | WO-91/12046 A1 | 8/1991 |
| WO | WO-92/19294 A1 | 11/1992 |
| WO | WO-94/02081 A1 | 2/1994 |
| WO | WO-94/09721 A1 | 5/1994 |
| WO | WO-94/09837 A1 | 5/1994 |
| WO | WO-94/13234 A1 | 6/1994 |
| WO | WO-96/20742 A1 | 7/1996 |
| WO | WO-98/23237 A1 | 6/1998 |
| WO | WO-98/30181 A1 | 7/1998 |
| WO | WO-99/26567 A1 | 6/1999 |
| WO | WO-00/06223 A1 | 2/2000 |
| WO | WO-00/64389 A1 | 11/2000 |
| WO | WO-00/64390 A1 | 11/2000 |
| WO | WO-00/64391 A1 | 11/2000 |
| WO | WO-00/64393 A1 | 11/2000 |
| WO | WO-00/64511 A1 | 11/2000 |
| WO | WO-01/078631 A2 | 10/2001 |
| WO | WO-01/78656 A2 | 10/2001 |
| WO | WO-01/097727 A1 | 12/2001 |
| WO | WO-02/036052 | 5/2002 |
| WO | WO-02/070045 A1 | 9/2002 |
| WO | WO-02/074052 A2 | 9/2002 |
| WO | WO-02/080811 A2 | 10/2002 |
| WO | WO-02/080829 A2 | 10/2002 |
| WO | WO-02/087418 A2 | 11/2002 |
| WO | WO-02/087479 A2 | 11/2002 |
| WO | WO-02/089699 A2 | 11/2002 |
| WO | WO-02/102274 A2 | 12/2002 |
| WO | WO-03/015659 A2 | 2/2003 |
| WO | WO-03/015667 A1 | 2/2003 |
| WO | WO-03/041622 A2 | 5/2003 |
| WO | WO-03/073968 A2 | 9/2003 |
| WO | WO-03/096871 A2 | 11/2003 |
| WO | WO-03/099175 A1 | 12/2003 |
| WO | WO-2004/014218 A2 | 2/2004 |
| WO | WO-2004/026347 A2 | 4/2004 |
| WO | WO-2004/043231 A2 | 5/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/073552 A2 | 9/2004 |
| WO | WO-2004/110391 A2 | 12/2004 |
| WO | WO-2005/016418 A1 | 2/2005 |
| WO | WO-2005/046782 A1 | 5/2005 |
| WO | WO-2005/055873 A2 | 6/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/036715 A2 | 4/2006 |
| WO | WO-2007/087061 A2 | 8/2007 |
| WO | WO-2007/115259 A2 | 10/2007 |
| WO | WO-2007/130393 A2 | 11/2007 |
| WO | WO-2008/061043 | 5/2008 |
| WO | WO-2009/012406 A1 | 1/2009 |
| WO | WO-2009/158517 A2 | 12/2009 |
| WO | WO-2009/158524 A2 | 12/2009 |

OTHER PUBLICATIONS

Bick MW "Use of tantalum for ocular drainage" Arch Ophthal. 42(4): 373-88 (1949).
Bietti "The present state of the use of plastics in eye surgery" Acta Ophthalmol (Copenh) 33(4):337-70 (1955).
Brown et al., "Internal Sclerectomy for Glaucoma Filtering Surgery with an Automated Trephine," Archives of Ophthalmology, 105:133-136 (1987).
Burchfield JC, Kass MA, Wax MB. Primary valve malfunction of the Krupin eye valve with disk. J Glaucoma. Jun. 1997;6(3):152-6.
Chiou et al. "Ultrasound biomicroscopy of eyes undergoing deep sclerectomy with collagen implant" Br J Ophthalmol 80 (1996), pp. 541-544.
Chylack LT, Bellows AR. Molecular sieving in suprachoroidal fluid formation in man. Invest Ophthalmol Vis Sci 17: 420, 1978.
Classen et al. "A histopathologic and immunohistorchemical analysis of the filtration bleb after unsuccessful glaucoma seton implantation" Am. J. Ophthalmol. 122:205-12 (1996).
Cohen et al. "First day post-operative review following uncomplicated phacoemulsification" Eye 12(4):634-6 (1998).
Collaborative Normal-Tension Study Group. Comparison of glaucomatous progression between untreated patients with normal-tension glaucoma and patients with therapeutically reduced intraocular pressures. Am J Ophthalmol 1998;126:487-97.
Congdon N, O'Colmain B, Klaver CC, et al. Causes and prevalence of visual impairment among adults in the United States. Arch Ophthalmol 2004;122:477-85.
Coote. "Glaucoma Hollow Fiber Filters—A New Glaucoma Seton. Preliminary Results." *J. Glaucoma.* vol. 8 No. 1 Supplement (1999):p. S4.
Cullen, et al. "Anterior Chamber of Frontal Sinus Shunt for the Diversion of Aqueous Humor: A Pilot Study in Four Normal Dogs". *Veterinary Ophthalmology.* vol. 1. No. 1. (1998):31-39.
Demailly et al. "Non-penetrating deep sclerectomy (NPDS) with or without collagen device (CD) in primary open-angle glaucoma: middle-term retrospective study" International Ophthalmology 20: 131-140, 1997.
Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].
Dinakaran et al. "Is the first post-operative day review necessary following uncomplicated phacoemulsification surgery?" Eye, 14(3A):364-6 (2000).
Draeger "Chirurgische Maβnahmen bei kongenitalem Glaukom" (Surgical Interventions in Congenital Glaucoma) Klin Monatsbl Augenheilkd 1993; 202(5): 425-427 [Article in German with English summary included].
Einmahl et al. "Evaluation of a novel biomaterial in the suprachoroidal space of the rabbit eye" Invest Ophthalmol Vis Sci. 43:1533-1539 (2002).
Ellis, RA "A Reduction of Intraocular Pressure Using Plastics in Surgery" Am J Ophth. 50; 1960, 733-742.
Emi et al. "Hydrostatic pressure of the suprachoroidal space" Invest. Ophthal. Visual Sci. 30(2):233-238 (1989).
Fanous MM, Cohn RA. Propionibacterium endophthalmitis following Molteno tube repositioning. J Glaucoma. Aug. 1997;6(4):201-2.

(56) References Cited

OTHER PUBLICATIONS

Friedman DS, Wolfs RC, O'Colmain BJ, et al. Prevalence of open-angle glaucoma among adults in the United States. Arch Ophthalmol 2004;122:532-8.
Fuchs E. "Detachment of the choroid inadvertently during cataract surgery" [German] von Graefes Arch Ophthalmol, 51:199-224 (1900) [Article in German with English summary].
G. Van Der Veen et al. "The Gonioseton, a surgical treatment for chronic glaucoma" Documenta Ophthalmologica Oct. 1990, vol. 75, Issue 3-4, pp. 365-375.
Gills et al. "Action of cyclodialysis utilizing an implant studied by manometry in a human eye" Exp Eye Res 1967; 6:75-78.
Gills JP "Cyclodialysis implants" South Med J. 1967 60(7):692-5.
Gills, "Cyclodialysis Implants in Human Eyes" Am J Ophth 61:1966,841-846.
Goldberg "Management of Uncontrolled Glaucoma With the Molteno System" Australian and New Zealand Journal of Ophthalmology 1987; 15: 97-107.
Gordon MO, Kass. MA, for the Ocular Hypertension Treatment Study Group. The Ocular Hypertension Treatment Study. Design and baseline description of the participants. Arch Ophthalmol 1999:573-83.
Grant, W.M., MD, Further Studies on Facility of Flow Through the Trabecular Meshwork, A.M.A. Archives of Ophthalmololgy, Oct. 1958, vol. 60, pp. 523-533.
Gross et al. "Surgical therapy of chronic glaucoma in aphakia and pseudophakia" Ophthalmology, 95:1195-201 (1988).
Harper SL, Foster CS. Intraocular lens explantation in uveitis. Int Ophthalmol Clin. 2000 Winter; 40(1):107-16.
Harrington "Cataract and Glaucoma. Management of the coexistent conditions and a description of a new operation combining lens extraction with reverse cyclodialysis." Am J Ophthalmol. May 1966;61(5 Pt 2):1134-40.
Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.
Heine I. "Cyclodialysis, a new glaucoma operation" [German] Dtsch Med Wochenschr, 31:824-826 (1905).
Hildebrand et al. "Efficacy of anterior chamber decompression in controlling early intraocular pressure spikes after uneventful phacoemulsification" J. Catact Refract Surg., 29:1087-92 (2003).
Hoskins, et al., "Aqueous Humor Outflow", Becker-Shaffer's Diagnosis and Therapy of the Glaucomas, 6th Edition, Chapter 4, pp. 41-66, 1989.
Howorth D J "Feasibility study for a micromachined glaucoma drainage device" Cranfield University School of industrial and manufacturing science MSc Thesis Academic Year 2001-2002 Sep. 13, 2002.
Hylton et al. "Update on prostaglandin analogs" Curr Opin Ophthalmol, 14:65-9 (2003).
In the Commonwealth of Australia—In the Matter of Australian Patent Application No. 2006336598 in the name of Transcend Medical, Inc. ("Applicant") and Opposition thereto by Glaukos Corporation ("Opponent"), Commonwealth of Australia—Opponent's Statement of Grounds and Particulars of Opposition. (Apr. 10, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Mr. Craig Andrews in support of Opponent's opposition. (Sep. 9, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Colin Clement in support of Opponent's opposition. (Sep. 9, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Ilesh Patel in support of Opponent's opposition. (Sep. 9, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Opponent's Amended Statement of Grounds and Particulars of Opposition. (Sep. 10, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Robert L. Stamper in support of Applicant's Evidence in Answer. (Dec. 4, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Jonathan G. Crowston in support of Applicant's Evidence in Answer. (Dec. 6, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Anne Jen-Wan Lee in support of Applicant's Evidence in Answer. (Dec. 7, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Colin Clement in support of Opponent's Evidence in Reply. (Feb. 8, 2015).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Ilesh Patel in support of Opponent's Evidence in Reply. (Feb. 10, 2015).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Mr. Craig Andrews in support of Opponent's Evidence in Reply. (Feb. 11, 2015).
Javitt JC, Chiang YP. Preparing for managed competition. Utilization of ambulatory eye care visits to ophthalmologists. Arch Ophthalmol 1993;111:1034-5.
Jay JL, Allan D. The benefit of early trabeculectomy versus conventional management in primary open-angle glaucoma relative to severity of disease. Eye 1989; 3:528-35.
Jordan J. "A Novel Approach to Suprachoroidal Drainage for the Surgical Treatment of Intractable Glaucoma" J. Glaucoma 15:200-205 (2006).
Karlen et al. "Deep sclerectomy with collagen implant: medium term results" Br. J. Ophthalmol, Jan. 1999, 83(1):6-11.
Kass MA, Heuer DK, Higginbotham EJ, et al for the Ocular Hypertension Treatment Study Group. The Ocular HypertensionTreatment Study. A randomized trial determines that topical ocular hypotensive medication delays or prevents the onset of primary open-angle glaucoma. Arch Ophthalmol 2002;120:701-13.
Klemm et al. "Die Ultraschallbiomikroskopie als Kriterium der Funktionsprüfung des suprachorioidalen Spaltes nach kammerwinkelchirurgischen Eingriffen ; (Ultrasound Biomicroscopic Imaging for Assessment of the Suprachoroidal Cleft after Angle Surgery)" Klinische Monatsblätter für Augenheilkunde 1997; 210: 74-77 [Article in German with English summary included].
Klemm et al. "Experimental use of space-retaining substances with extended duration: functional and morphological results" Graefes Arch Clin Exp Ophthalmol Sep. 1995; 233(9):592-7.
Krejci "Cyclodialysis with hydroxymethyl methacrylate capillary strip (HCS). Animal experiments with a new approach in glaucoma drainage surgery" Ophthalmologica 1972; 164(2):113-21.
Krejci L. "Microdrainage of anterior chamber of eye glaucoma operation using hydron capillary drain." Acta Univ Carol Med Monogr. 1974;(61):1-90.
Kupfer "Studies on intraocular pressure. I. A technique for polyethylene tube implantation into the anterior chamber of the rabbit." Arch Ophthalmol. Apr. 1961;65:565-70.

(56) References Cited

OTHER PUBLICATIONS

La Rocca "Gonioplasty in Glaucoma*A Preliminary Report" Br J Ophth 46:1962, 404-415.

Law et al., "Retinal Complications After Aqueous Shunt Surgical Procedures for Glaucoma" Arch Ophthal.; Dec. 1996; vol. 114:1473-1480.

Lee et al. "Aqueous-venous shunt and intraocular pressure. Preliminary report of animal studies." *Investigative Ophthalmology.* vol. 5 No. 1: 59-64. Feb. 1966.

Lee et al. "Magnetic resonance imaging of the aqueous flow in eyes implanted with the trabeculo-suprachoroidal glaucoma seton" Invest. Ophthalmol. Vis. Sci. 33:948 (1992).

Lee KY. Trabeculo-suprachoroidal shunt for treating recalcitrant and secondary glaucoma. Presented at the American Academy of Ophthalmology Annual Meeting, Anaheim, CA, 1991.

Leske MC, Heijl A, Hussein M, et al for the Early Manifest Glaucoma Trial Group. Factors for glaucoma progression and the effect of treatment. The Early Manifest Glaucoma Trial. Arch Ophthalmol Jan. 2003;121:48-56.

Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.

Losche W. "Proposals for improvement of cyclodialysis" Klin Monatsblatter Augenheilkd Augenarztl Fortbild 121(6):715-6 (1952) [German].

Marx et al., "Use of the Ganciclovir Implant in the Treatment of Recurrent Cytomegalovirus Retinitis" Arch Ophthal.; Jul. 1996; vol. 114:815-820.

McPherson "Combined Trabeculotomy and Cataract Extraction as a Single Operation*" Tr. Am. Ophth. Soc., vol. LXXIV, 1976; 251-260.

Migdal C, Gregory W, Hitchings R. Long term functional outcome after early surgery compared with laser and medicine in open-angle glaucoma. Ophthalmology 1994;101:1651-7.

Miglior S, Pfeiffer N, Zeyen T et al for the European Glaucoma Prevention Study Group. Results of the European Glaucoma Prevention Study. Ophthalmology 2005;112:366-75.

Miglior S, Zeyen T, Pfeiffer N, et al for the European Glaucoma Prevention Study Group. The European Glaucoma Prevention Study design and baseline description of the participants. Ophthalmology 2002;109:1612-21.

Miki, MD et al., "Intraocular Cannula for Continuous, Chronic Drug Delivery—Histopathic Observations and Function" Arch Ophthal.; May 1985; vol. 103:712-717.

Molteno et al. "Long tube implants in the management of glaucoma" South African Medical Journal, Jun. 26, 1976;50(27):1062-6.

Molteno et al. "The Vicryl tie technique for inserting a draining implant in the treatment of secondary glaucoma." Australian and New Zealand Journal of Ophthalmology 1986; 14: 343-354.

Moses RA "Detachment of ciliary body-anatomical and physical considerations" Investigative Ophthalmology & Visual Science, Assoc. for Research in Vision and Ophthalmology, US, vol. 4, No. 5, Oct. 1, 1965.

Nesterov AP et al. "Surgical stimulation of the uveoscleral outflow. Experimental studies on enucleated human eyes" Acta Opthalmol (Copenh) June; 57(3):409-17 (1979).

Nguyen et al., "Complications of Baerveldt Glaucoma Drainage Implants" Arch Ophthal.; May 1998; vol. 116:571-575.

Noecker RJ. Clinical Evaluation of a Novel Gold Micro-Shunt for Reduction of 10 P in Refractory Glaucomas. American Glaucoma Society Annual Meeting, San Francisco, CA, 2007.http://www.glaucomaweb.org/associations/5224/files/AGS%20AM07%20Prgrm%20FINAL.pdf. Accessed Nov. 1, 2008).

O'Brien et al. "Cyclodialysis" Arch Ophthal. 1949;42(5):606-619.

Odrich. "The New Technique During Complex Tube-Shunt Implantation". *J. Glaucoma.* vol. 9 No. 3 (2000):278-279.

Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.

Ozdamar et al. "Suprachoroidal seton implantation in refractory glaucoma: a novel surgical technique" J. Glaucoma Aug. 2003; 12(4):354-9.

Pinnas G. et al. "Cyclodialysis with teflon tube implants" Am J. Ophthalmol Nov. 1969; 68(5):879-883.

Portney GL, "Silicone elastomer implantation cyclodialysis." Arch Ophthalmol 1973; 89: 10-12.

Pruett et al., "The Fishmouth Phenomenon-II. Wedge Scleral Buckling" Arch Ophthal.; Oct. 1977; vol. 95:1782-1787.

Qadeer "Acrylic Gonio-Subconjunctival Plates in Glaucoma Surgery" Br J Ophthalmol. Jun. 1954; 38(6): 353-356.

Quigley HA, Vitale S. Models of open-angle glaucoma prevalence and incidence in the United States. Invest Ophthalmol Vis Sci 1997; 38:83-91.

Richards et al. "Artificial Drainage Tubes for Glaucoma" Am J Ophth 60:1965,405-408.

Ritch, et al., "Uveoscleral Outflow", The Glaucomas. St. Louis: Mosby, 1996; pp. 337-343.

Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.

Rosenberg, et al. "Implants in glaucoma surgery" Chapter 88, The Glaucomas, Ritch et al. Eds. 2nd Ed. Mosby St. Louis 1996; p. 1783-1807.

Row H. "Operation to control glaucoma: preliminary report" Arch. Ophthal 12:325 (1934).

Rowan, Patrick J., MD, Combined Cyclodialysis and Cataract Surgery, Ophthalmic Surgery and Lasers, Dec. 1998, vol. 29, No. 12, pp. 962-968 (9 pages).

Sampimon "A New Approach to Filtering Glaucoma Surgery" Ophthalmologica (Basel) 151: 1966, 637-644.

Schappert S. Office visits for glaucoma: United States, 1991-92. Advance data from vital and health statistics. vol. 262. Hyattsville, MD: National Center for Health Statistics, 1995.

Schocket, Stanley S. "Investigations of the Reasons for Success and Failure in the Anterior Shunt-To-The-Encircling-Band Procedure in the Treatment of Refractory Glaucoma." *Tr. Am. Ophth. Soc.* vol. LXXXIX. (1986):743-798.

Shaffer RN, Weiss DI. Concerning cyclodialysis and hypotony. Arch Ophthalmol 68: 25, 1962.

SOLX Clinical Literature Handout; Industry Show Feb. 2006; "The SOLX Gold Micro-shunt (GMS) treatment".

Sommer A, Tielsch JM, Katz J, et al. Racial differences in the cause-specific prevalence of blindness in east Baltimore. N Engl J Med 1991;325:1412-7.

Sourdille et al. "Reticulated hyaluronic acid implant in non-perforating trabecular surgery." J Cataract Refract Surg 25: 332-339. (1999).

Spiegel et al. "Schlemm's Canal Implant: A New Method to Lower Intraocular Pressure in Patients With POAG?" *Ophthalmic Surgery and Lasers.* vol. 30, No. 6: 492-494. Jun. 1999.

Srinivasan et al. "Microbial contamination of the anterior chamber during phacoemulsification" J. Cataract Refract Surg. 28:2173-6 (2002).

Suguro K, Toris CB, Pederson JE. Uveoscleral outflow following cyclodialysis in the monkey eye using a fluorescent tracer. Invest Ophthalmol Vis Sci 1985: 26, 810.

The Advanced Glaucoma Intervention Study (AGIS): 7. The relationship between control of intraocular pressure and visual field deterioration. The AGIS Investigators. Am J Ophthalmol 2000;130:429-40.

The Advanced Glaucoma Intervention Study (AGIS); 13. Comparison of treatment outcomes within race: 10-year results. Ophthalmology 2004;111:651-64.

The Glaucoma Laser Trial (GLT) and Glaucoma Laser Trial Follow-up Study: 7. Results. Am J Ophthahnol 1995;120:718-31.

The Glaucoma Laser Trial (GLT). 2. Results of argon laser trabeculoplasty versus topical medicines. The Glaucoma Laser Trial Research Group. Ophthalmology 1990;97:1403-13.

(56) References Cited

OTHER PUBLICATIONS

Tielsch JM, Sommer A, Katz J, et al. Racial variations in the prevalence of primary open-angle glaucoma. The Baltimore Eye Survey. JAMA 1991;266:369-74.

Toris CB. Extravascular albumin concentration of the uvea. Invest Ophthalmol Vis Sci 1990; 31:43.

Toris et al. "Aqueous humor dynamics in the aging human eye" Am J. Ophthalmol., 127:407-12 (1999).

Toris et al. "Effect of intraocular pressure on uveoscleral outflow following cyclodialysis in the monkey eye." Investigative Ophthalmology & Visual Science. 26 (1985) 1745-1749.

*Transcend Medical Inc. v. Glaukos Corporation*, Transcend Medical, Inc.'s Disclosures Pursuant to Default Discovery Rule 4 (d) (United States District Court for the District of Delaware, dated Dec. 6, 2013; case No. C.A. No. 13-830 (MSG) and Certificate of Service, dated Dec. 9, 2013.

Trigler L, Proia AD, Freedman SF. Fibrovascular ingrowth as a cause of Ahmed glaucoma valve failure in children. Am J Ophthalmol. Feb. 2006;141(2):388-9.

Troncoso Manuel U., "Cyclodialysis with insertion of metal implant in treatment of glaucoma, A Preliminary Report" Arch. Ophthal. 23:270 (1940).

Troncoso, Manuel U., Tantalum implants for inducing hypotny, Am Journal of Ophthalmology, vol. 32(4):499-508 (1949).

Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.

Wamsley S, Moster MR, Rai S, Alvim HS, Fontanarosa J. Results of the use of the Ex-PRESS miniature glaucoma implant in technically challenging, advanced glaucoma cases: a clinical pilot study. Am J Ophthalmol. Dec. 2004; 138(6): 1049-51.

Yablonski, "Some thoughts on the pressure dependence of uveoscleral flow" Journal of Glaucoma, 12(1):90-92 (2003).

Yablonski, "Trabeculectomy with Internal Tube Shunt: a novel glaucoma surgery" J. Glaucoma 14:91-97 (2005).

Zhou et al. "A trabecular bypass flow hypothesis" J Glaucoma. 14(1):74-83 (2005).

\* cited by examiner

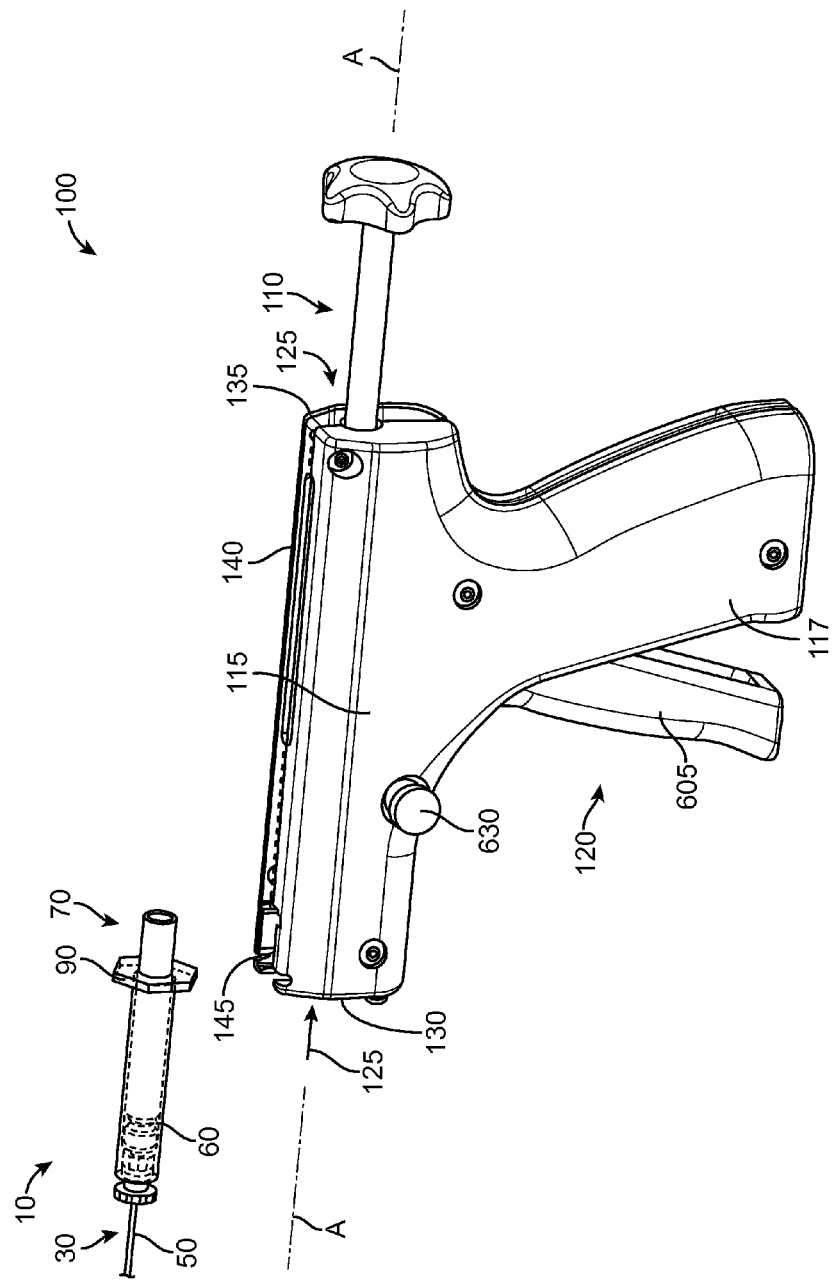

DEVICE FOR DISPENSING INTRAOCULAR SUBSTANCES

CROSS-REFERENCE TO RELATED APPLICATION

This application claims priority to U.S. Provisional Patent Application Ser. No. 61/812,606, titled "Device for Dispensing Intraocular Substances," filed Apr. 16, 2013, the disclosure of which is hereby incorporated by reference in its entirety herein. Priority of the aforementioned filing date is claimed.

BACKGROUND

During ophthalmic surgeries, fluids are injected into the eye for various purposes. Viscoelastic substances may be injected into the eye to open the anterior chamber and allow working room for the surgeon within the chamber. Viscoelastic substances may also be injected into other structures to allow the structures to remain patent post-operatively. For example, viscoelastic may be injected into the Schlemm's Canal in a procedure called a 'viscocanalostomy' or a 'canaloplasty'. Viscoelastic may also be injected into the suprachoroidal space to maintain a cleft. These procedures may be done in conjunction with an implant or as a separate procedure.

SUMMARY

Disclosed herein are devices, systems and methods for intraocular delivery of materials from a container.

In one aspect, disclosed is an injection device having a housing configured to reversibly couple to a container holding a material; a plunger moveably coupled to a piston and configured to move a distance into the container; a spring element; and a trigger mechanism coupled to the housing and configured to move the plunger the distance.

The device can further include an adjustment mechanism slideably positioned within the housing. The spring element can be coupled to the adjustment mechanism. The trigger mechanism can be configured to actuate the adjustment mechanism to apply a force to move the plunger the distance. The plunger can move axially along a given length within the piston. The plunger can include a proximal end region and a distal end region. The proximal end region of the plunger can include an elongate slot. The piston can include a distal opening to a bore through which the proximal end region of the plunger is configured to insert. The piston can include sidewalls having a pair of openings configured to align with the elongate slot of the plunger. The spring element can be positioned within the bore of the piston between the proximal end region of the plunger and a distal end of the bore. The spring element can be configured to apply a spring force counter to the force applied to move the plunger the distance preventing the force to move the plunger from exceeding a threshold maximum force. The spring element can press on the proximal end region of the plunger and causes the plunger to move distally. The spring element can compress between the proximal end region of the plunger and the distal end of the piston bore when a force within the container is above the force of the spring element. The trigger mechanism can prevent the adjustment mechanism from moving in a rearward proximal direction and allows free movement of the adjustment mechanism in a forward distal direction. The trigger mechanism can include a rotating handle and a pivoting latch constrained by the rotating handle. The piston can include a lower surface having a plurality of notches. The pivoting latch can be configured to engage with one notch of the plurality of notches on the lower surface of the piston. The rotating handle can rotate relative to the housing towards a piston grip handle. The pivoting latch can push against the one notch when the rotating handle rotates moving the adjustment mechanism the distance. The housing can include an upper surface having a slot through which the container is loaded. The container can include a barrel, a stopper slideably disposed within the barrel, and an outlet. The outlet can remain external to the housing when the container is loaded in the slot. The plunger can have a distal end that reversibly engages a proximal end of the stopper. The stopper can include a notch in the proximal end and the plunger can include a projection from the distal end. The projection and notch can have corresponding shapes. The container can contain a viscoelastic material. A metered volume of the material can be delivered from the container with each actuation of the trigger mechanism. The metered volume can depend upon the distance and a cross-sectional area of the container.

In an interrelated aspect, disclosed is an injection device including a plunger configured to advance a distance into a container holding a material; a pushing mechanism configured upon movement of the pushing mechanism to apply a force to a spring element; and the spring element configured to apply the force to the plunger and which is configured to dampen the distance moved by the pushing mechanism from the distance moved by the plunger.

A user may impart a force on the pushing mechanism and therein cause the pushing mechanism to move a predetermined distance toward the plunger. The spring element can exist between the plunger and the pushing mechanism such that the pushing mechanism contacts the spring element which in turn contacts the plunger. As the pushing mechanism advances forward it applies a force onto the spring element which in turn applies the force on the plunger.

The plunger in turn applies the force on a moveable stopper within the container of the material such that the pressure of the material within the container increases. The material may then exit through an outlet of the container. The outlet of the container can be connected to a small delivery lumen tubing which can require high pressure for the material to flow, particularly viscous materials.

The spring element can be, for example, a compression spring that is axially constrained with a given threshold force. When the force applied by the pushing mechanism is less than the spring threshold force, the spring does not compress further and the distance traveled by the pushing mechanism is the same over time as the distance traveled by the plunger. However, if the force necessary by the plunger to expel the material from the container is higher than the threshold force, the spring element compresses and the distance traveled by the pushing mechanism may not be the same as the distance traveled by the plunger over time. For example, the pushing mechanism may move a distance of 0.030" in 2 seconds, while the plunger may move the same distance of 0.030" but in a time of 5 seconds. In this example, the material exits the outlet of the container over a longer period of time at a slower rate and therefore the peak pressure reached in the container may be less than if no spring element was present.

In an embodiment, he plunger can move axially along a given length within a piston. The plunger can include a proximal end region and a distal end region. The proximal end region of the plunger can include an elongate slot. The piston can include a distal opening to a bore through which the proximal end region of the plunger is configured to insert. The piston can include sidewalls having a pair of openings configured to align with the elongate slot of the plunger. The spring element coupled to the plunger can be positioned within the bore of the piston between the proximal end region of the plunger and a distal end of the bore. The spring element can press on the proximal end region of the plunger and cause the plunger to move distally. The spring element can compress between the proximal end region of the plunger and the distal end of the piston bore when a force within the container is greater than the second force of the spring element. The trigger mechanism can include a rotating handle and a pivoting latch constrained by the rotating handle. The piston can include a lower surface having a plurality of notches. The pivoting latch can be configured to engage with one notch of the plurality of notches on the lower surface of the piston. The rotating handle can rotate relative to the housing towards a piston grip handle. The pivoting latch can push against the one notch when the rotating handle rotates moving the adjustment mechanism the distance. The housing can include an upper surface having a slot through which the container is loaded. The container can include a barrel, a stopper slideably disposed within the barrel, and an outlet. The outlet can remain external to the housing when the container is loaded in the slot. The plunger can have a distal end that reversibly engages a proximal end of the stopper. The stopper can include a notch in the proximal end and the plunger can include a projection from the distal end. The projection and notch can have corresponding shapes. The container can contain a viscoelastic material. A metered volume of the material can be delivered from the container with each actuation of the trigger mechanism. The metered volume can depend upon the distance and a cross-sectional area of the container.

More details of the devices, systems and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity FIG. 1A shows an isometric view of an implementation of an injection device and a container;

DETAILED DESCRIPTION

This disclosure relates generally to methods and devices for dispensing intraocular substances. In particular, described are methods and devices for dispensing metered doses of a material, such as viscoelastic substances, into an eye at metered doses within a given force range or below a given force limit. U.S. patent application Ser. No. 11/615, 810 filed Dec. 22, 2006 and entitled GLAUCOMA TREATMENT DEVICE is incorporated herein by reference in its entirety.

Viscoelastic substances generally can be supplied in prepackaged containers. The containers can include a syringe and plunger where a user can manually press the plunger on the syringe vial to dispense the viscoelastic through a distal outlet. Manually pressing the plunger can be difficult to control and can result in inaccuracies in the measured amount of material dispensed from the syringe vial. The syringe vial can have gradations and markings to aid the user for measuring the amount of material dispensed. These markings can still be problematic when it is desired to deliver small quantities. Further, intraocular delivery of material to very small structures such as in the eye can require instrumentation having very small lumen size. The force required to inject material through these small lumens is relatively high and can be difficult for a user to manually depress the syringe plunger. Additionally, injection of materials at high pressures may not be desirable, since exemplary tissue structures can be delicate and high pressure or velocity injection can damage the structures. Other injection devices may exist which provide metered dosing of material and offer a mechanical advantage to the user such that the activation force is reduced. However, these can allow the user to inject materials at higher pressures and velocities than may be desirable. An injection device which includes metered dosing and which limits the pressure and velocity of the injected materials would be useful.

Although the injection devices herein are described in the context of injecting viscoelastic material from a container into the eye, it should be appreciated that the injection device can be useful for the injection of a variety of materials or drugs to a variety of locations within a patient. For example, precise volumes of a balanced saline solution (BSS) can be injected into the eye during a variety of ophthalmic procedures. Additionally, precise amounts of drug can be injected into the eye or other locations during surgical procedures or for therapeutic treatments, for example, alcohol ablation of cardiac tissue in which metered dose of alcohol are desired.

Figure 1B:
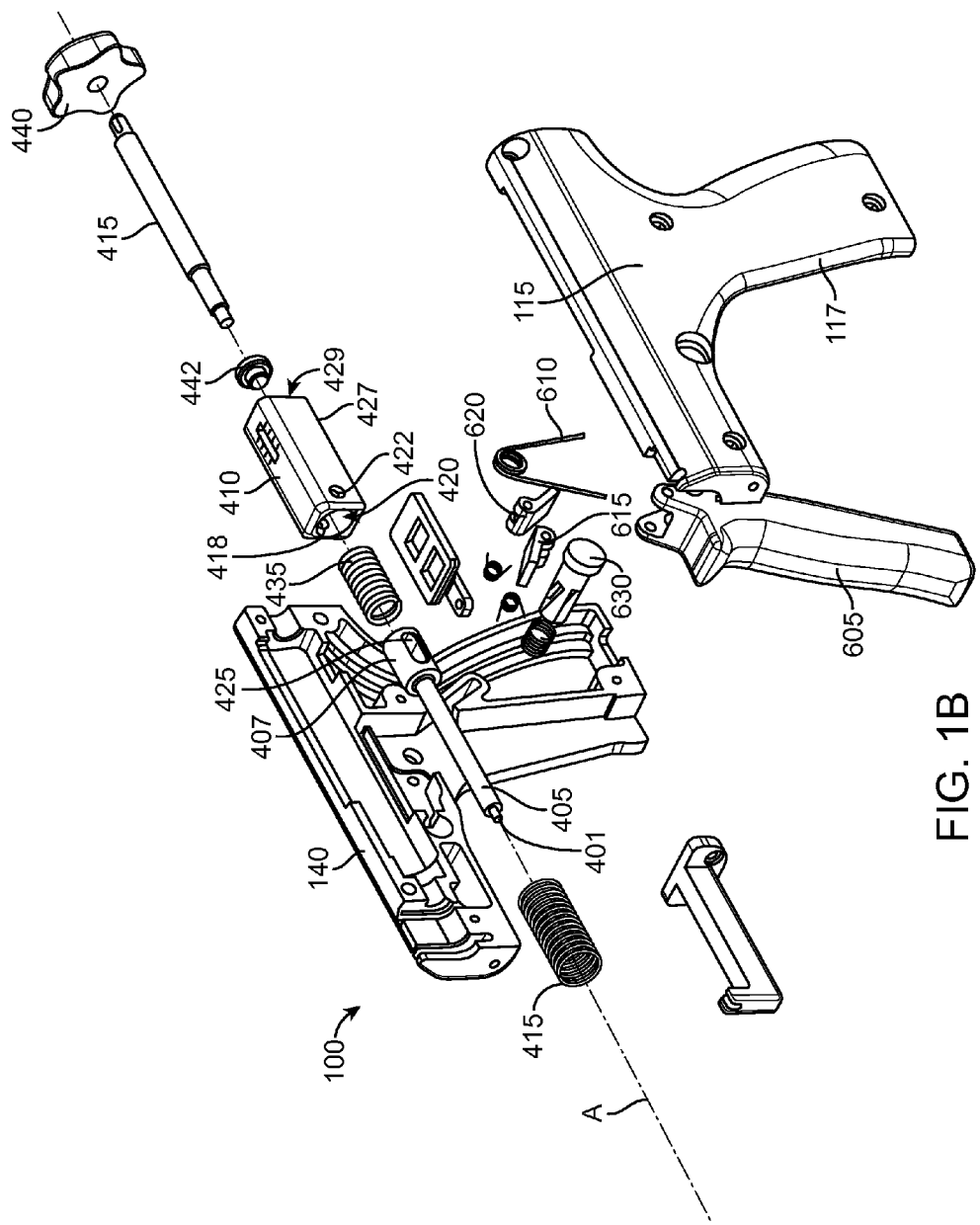
FIG. 1B shows an exploded view of the injection device of FIG. 1A.
Figure 2:
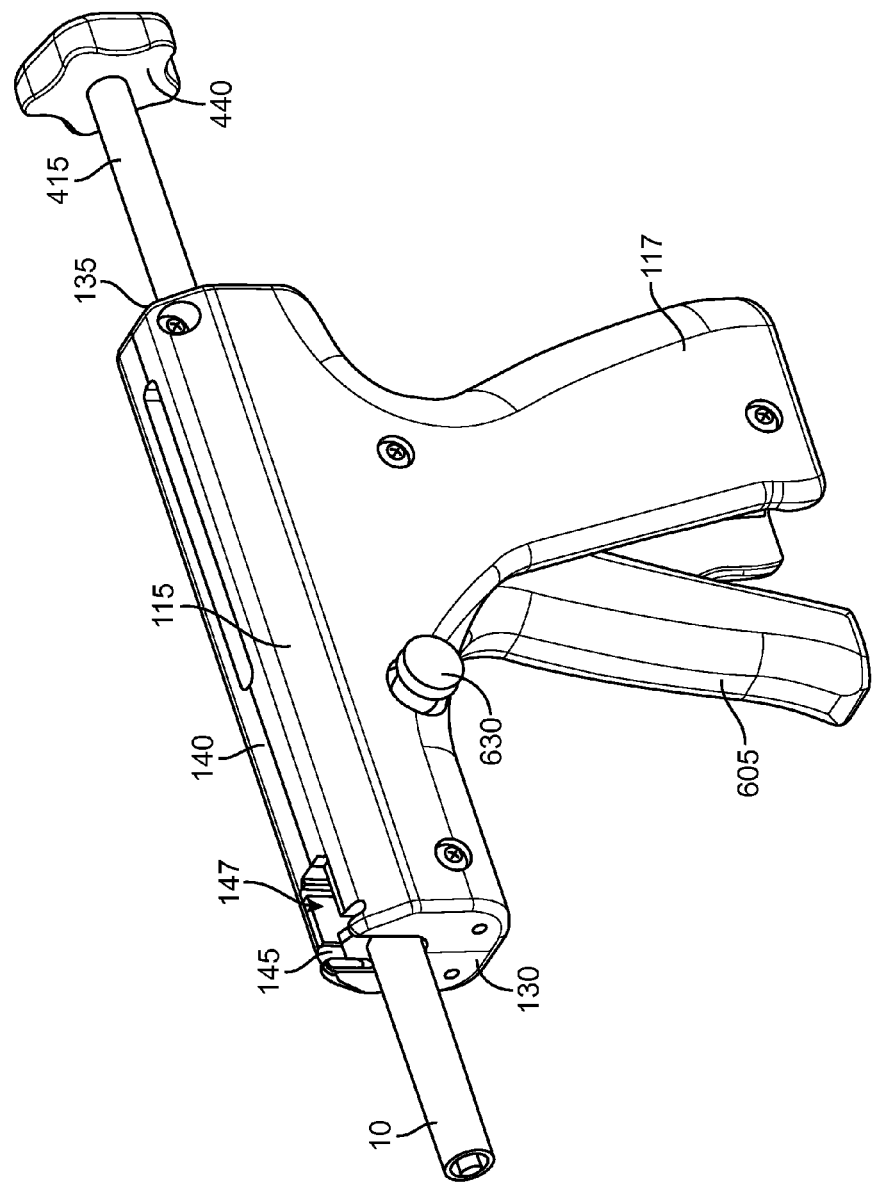
FIG. 2 shows an isometric view of the injection device of FIG. 1A having the container loaded.
Figure 3:
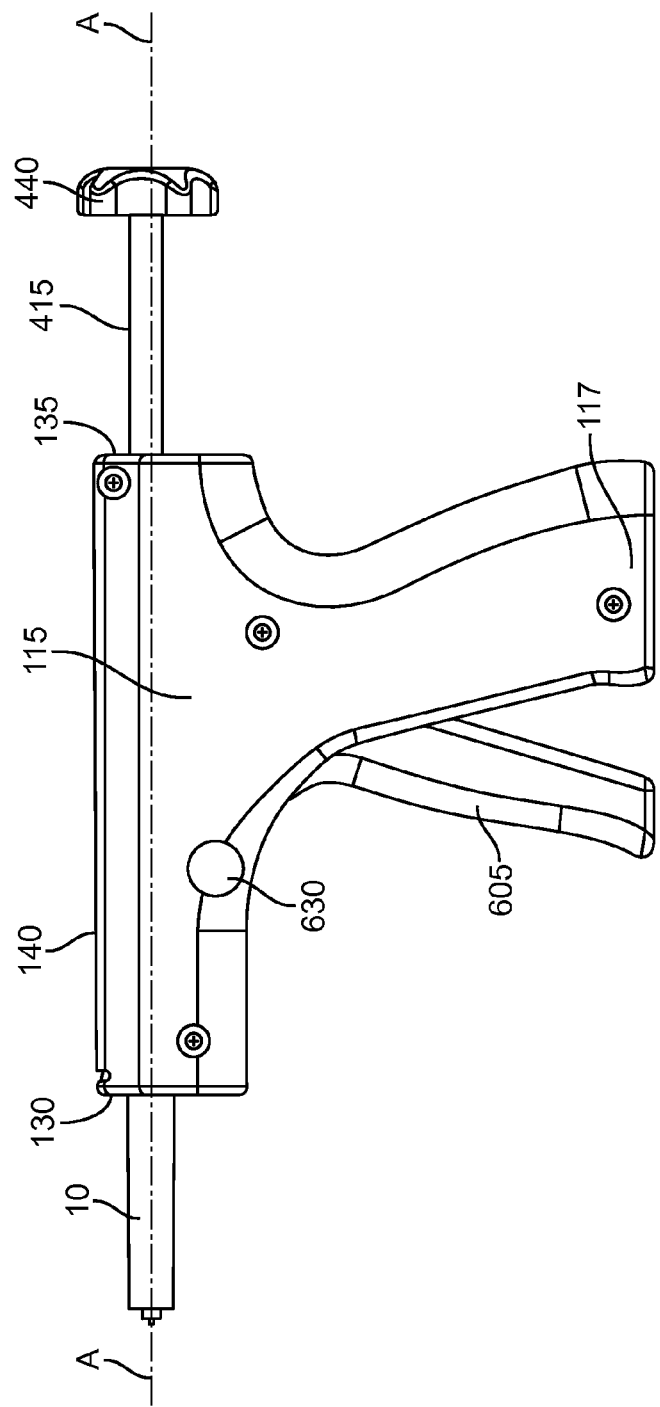
FIG. 3 shows a side view of the injection device and the loaded container of FIG. 2.

FIGS. 1A-1B illustrate an implementation of an injection device 100 that can be used to deliver material from a container 10. The injection device 100 can include an adjustment or pushing mechanism 110, a housing 115, and a spring element. FIG. 1A shows the injection device 100 having a container 10 about to be loaded and FIGS. 2 and 3 show the injection device 100 with the container 10 loaded into the housing 115.

The container 10 can be a syringe-type container having a distal end region 30, a proximal end region 70 and a barrel 60 within which liquid material can be contained and through which a stopper 20 (see FIGS. 4, 5, and 6) can slide to expel the material from the barrel 60 through a distal outlet 40 in the distal end region 30 of the container 10. The distal outlet 40 can have a needle 50 attached (see FIG. 1A).

The proximal end region 70 of the container 105 can include a flange 90. The container 10 can be a viscoelastic container having a variety of container types including any commercially-available viscoelastic product used for ophthalmic surgeries such as HEALON 5 (AMO), HEALON GV (AMO), PROVISC (Alcon), or the like, which are typically sold in a syringe vial used for the injection of the material.

Additionally other materials may be commixed for delivery. For example, the viscoelastic substance may be mixed with pharmaceutical agents such as antiproliferative drugs, steroids, or any other drug. In this embodiment, the drug mixed with the viscoelastic material may release over a longer period of time than if the drug was injected without mixing it with the viscoelastic.

Again with respect to FIG. 1A, the housing 115 of the injection device 100 can include a bore 125 that can extend from near a distal end 130 of the housing 115 towards a proximal end 135 of the housing 115. The housing 115 can accept at least a portion of the container 10 within a slot 147 near a distal end 130 of the housing 115 that can align with the bore 125. The slot 147 can be available from an upper surface 140 of the housing 115 such that the container 10 can be loaded in a top-down direction into the housing 115. In this implementation, the slot 147 can include a grooved fitting 145 through which the flange 90 of the proximal end region 70 of the container 10 can be inserted such that the barrel 60 is co-axially aligned with a longitudinal axis A of the bore 125. In an alternative embodiment, the slot 147 can be available from another surface such as a side surface or the bottom surface. Additionally, a latching mechanism can be used that has an open and closed state to allow the container 10 to be inserted into the slot 147 and then prevented from coming out when the latching mechanism is in a closed state. The distal outlet 40 of the distal end region 30 of the container 10 (and needle 50, if present) can remain external to the distal end 130 of the housing 115 such that it is available for tissue injection.

Figure 4:
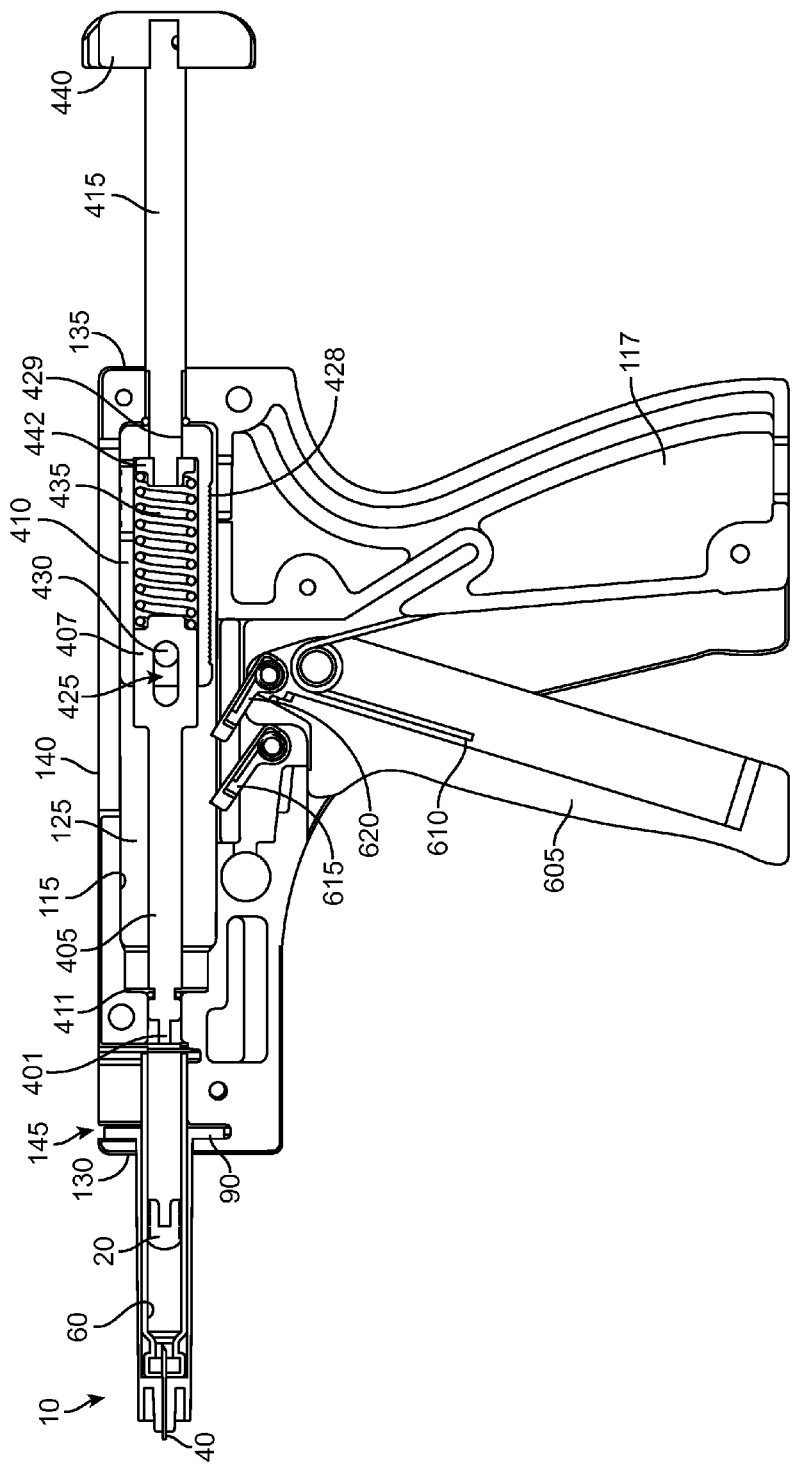
FIG. 4 shows a cross-section of the injection device and the loaded container of FIG. 3.
Figure 5:
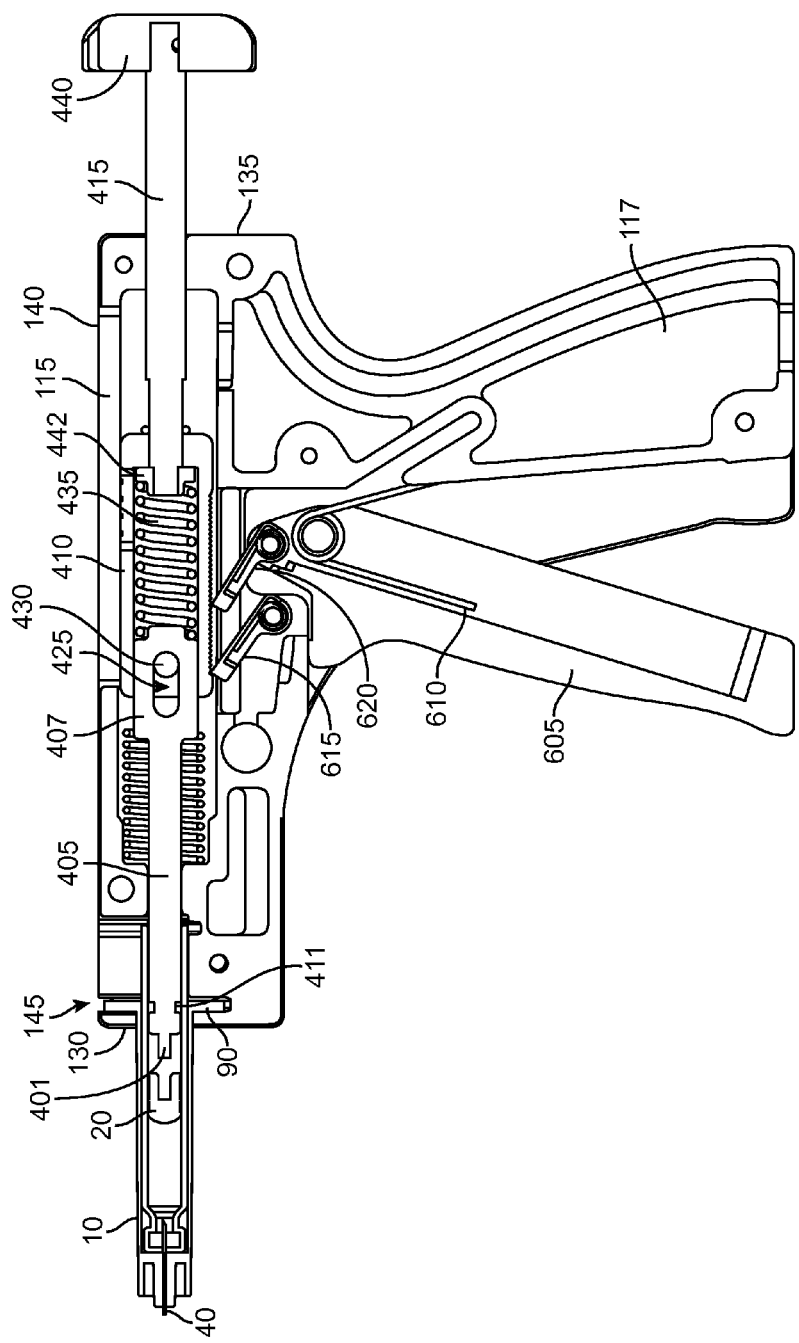
FIG. 5 shows a cross-section of the injection device and the loaded container of FIG. 3 in a different delivery state.

As mentioned above, the injection device 100 can include a pushing mechanism 110 to dispense material from within a container 10 slideably positioned within the bore 125 of the housing 115. As best shown in FIG. 1B and FIG. 4, the pushing mechanism 110 can include a plunger 405, an advancing block 410, and an adjustment element, such as an adjustment rod 415 that extends co-axially aligned with the longitudinal axis A through the housing 115 along at least a portion of the bore 125. The plunger 405 can be positioned within the bore 125 extending distal to the advancing block 410, which can extend distal to the adjustment rod 415, which can extend out the proximal end 135 of the housing 115. As will be described in more detail below, the plunger 405 can extend out of the bore 125 into the slot 147 of the housing in order to insert through a proximal end region of the container 10 to interface with the stopper 20 slideably disposed within the barrel 60 of the container 10 to dispense material out the distal outlet 40.

Still with respect to FIG. 1B and FIG. 4, the adjustment rod 415 can be an elongate element having a distal end region and a proximal end region. The adjustment rod 415 can extend co-axially along the longitudinal axis A of the bore 125. The distal end region of the rod 415 can insert through the proximal end 135 of the housing 115 into bore 125. The distal end region of the rod 415 can include threaded feature(s) that engage with the bore 125 allowing the rod 415 to be screwed into and out of the bore 125 as the rod 415 is turned. There, the distal end region of the adjustment rod 415 can insert through and couple with a proximal end region of the adjustment block 410 via washer element 442. The proximal end region of the rod 415 can remain external to the housing 115 and available to a user from outside the housing 115. The proximal end region of the rod 415 can include a knob 440 that can be rotated by the user to advance the adjustment rod 415 in a distal direction. Rotation of the knob 440 by a user can result in the adjustment rod 415 moving distally relative to the adjustment block 410.

Figure 7:
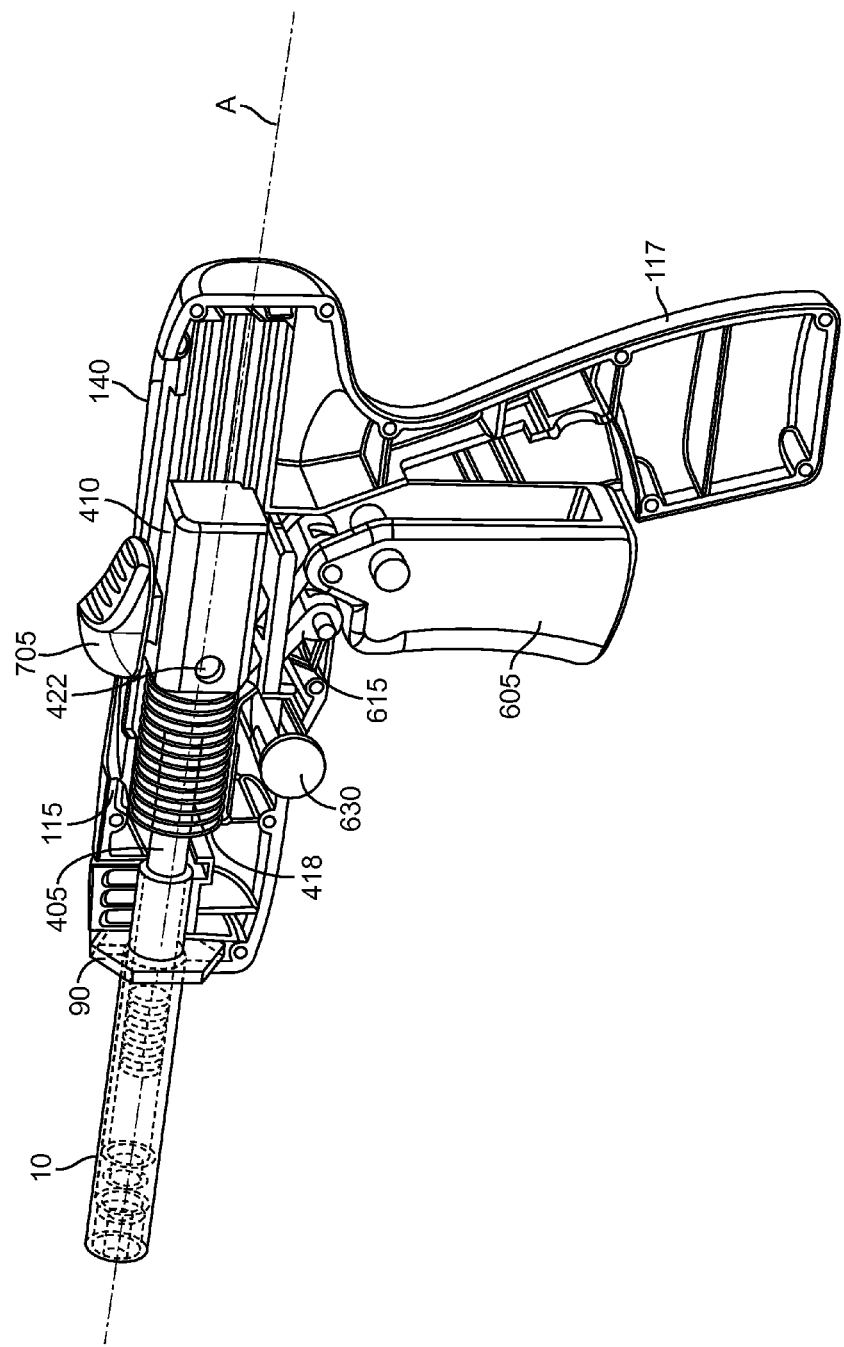
FIG. 7 shows a cross-section of another implementation of an injection device having a container loaded therein.

It should be appreciated that the injection device need not include an adjustment rod 415 extending co-axially with longitudinal axis A within the bore 125 of the housing 115. As shown in FIG. 7, the injection device can include an adjustment element that includes a sliding actuator 705 attached to a surface of the advancing block 410, such as an upper surface, such that the sliding actuator 705 extends along an axis that is orthogonal to the longitudinal axis A. The sliding actuator 705 can be accessible to a user via an elongate channel in the upper surface 140 of the housing 115. The sliding actuator 705 can be used to manually withdraw the plunger 405 from the proximal end region 70 of the container 10 or manually engage the plunger 405 with the proximal end region 70 of the container 10.

Figure 8:
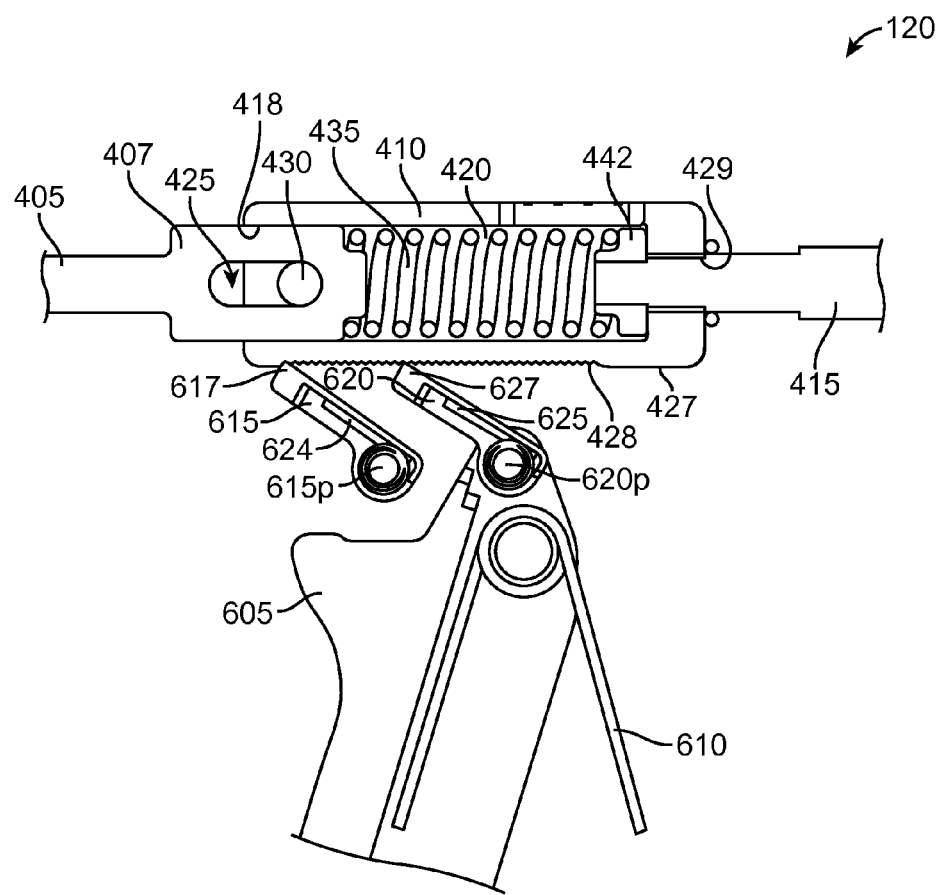
FIGS. 8, 9, and 10 show isolated side views of an implementation of a trigger mechanism.
Figure 9:
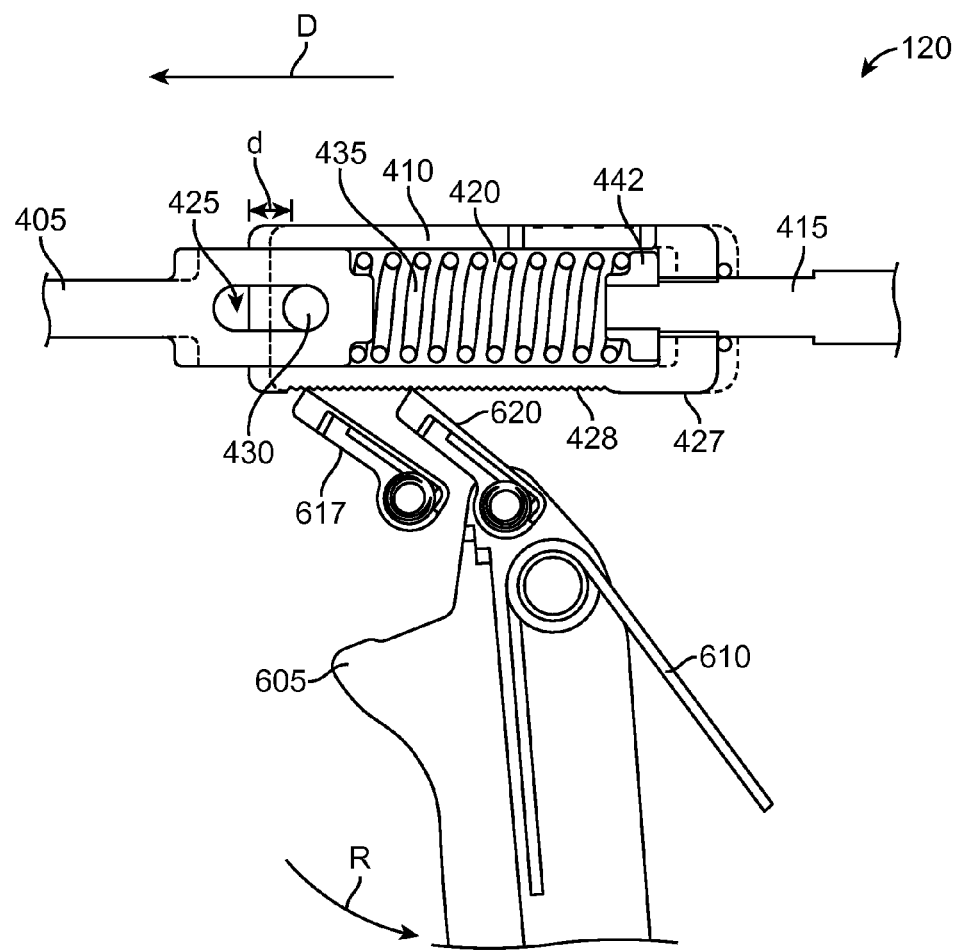

Again with respect to FIG. 1B and FIG. 4, the advancing block 410 can be an element extending along the longitudinal axis A of and within the bore 125. The advancing block 410 can include a distal opening 418 to a bore 420. The opening 418 and bore 420 can be configured to couple with a proximal end region 407 of the plunger 405. The sidewalls of the advancing block 410 can include a pair of openings 422 aligned opposite one another across the bore 420 and configured to align with a slot 425 through the proximal end region 407 of the plunger 405 as will be described in more detail below. A lower surface 427 of the advancing block 410 can have a series of notches 428 (best shown in FIGS. 8, 9, and 10). The proximal end region of the advancing block 410 can include an opening 429 into the bore 420 through which the distal end of the adjustment rod 415 can be inserted to connect with washer element 442 positioned within the bore 420, as described above. An advancing block spring 435 can be positioned within the bore 420 of the advancing block 410 between the proximal end region 407 of the plunger 405 and the distal end region of the bore 420 against the adjustment rod 415.

Still with respect to FIG. 1B and FIG. 4, the plunger 405 can be an elongate element extending along the longitudinal axis A of and within the bore 125. The plunger 405 can have a distal end region 401 and a proximal end region 407. As described above, the proximal end region 407 of the plunger 405 can be configured to insert through the distal opening 418 in the advancing block 410 into bore 420. The outer surface of the proximal end region 407 of the plunger 405 can have a shape that corresponds to the shape of the bore 420, which can be cylindrical or another suitable geometry. The proximal end region 407 of the plunger 405 can have a slot 425 extending through the proximal end region 407 that is configured to align with the pair of openings 422 in the sidewalls of the advancing block 410. The slot 425 and openings 422 can receive a dowel pin 430 therethrough. This arrangement can allow for the plunger 405 to move axially along a given length within the bore 420 of the advancing block 410 before the dowel pin 430 bottoms out against the proximal end of the slot 425. It should be appreciated that the elongate slot need not extend through the entire proximal end region. Rather, the proximal end region 407 also can have a pair of elongate channels configured to align with the pair of openings 422 that in turn, receive a pair of pins 430.

The plunger 405, advancing block 410 and adjustment rod 415 can be retracted towards the proximal end 135 of the housing 115 to allow a container 10 to be inserted within the slot 147 (see FIG. 2). Upon loading a container 10 into the slot 147, the plunger 405 can be advanced distally by actuation of the adjustment mechanism 110 out of the bore 125 the proximal end region of the container 10 positioned within the slot 147 to contact the stopper 20 (see FIG. 5).

Figure 6:
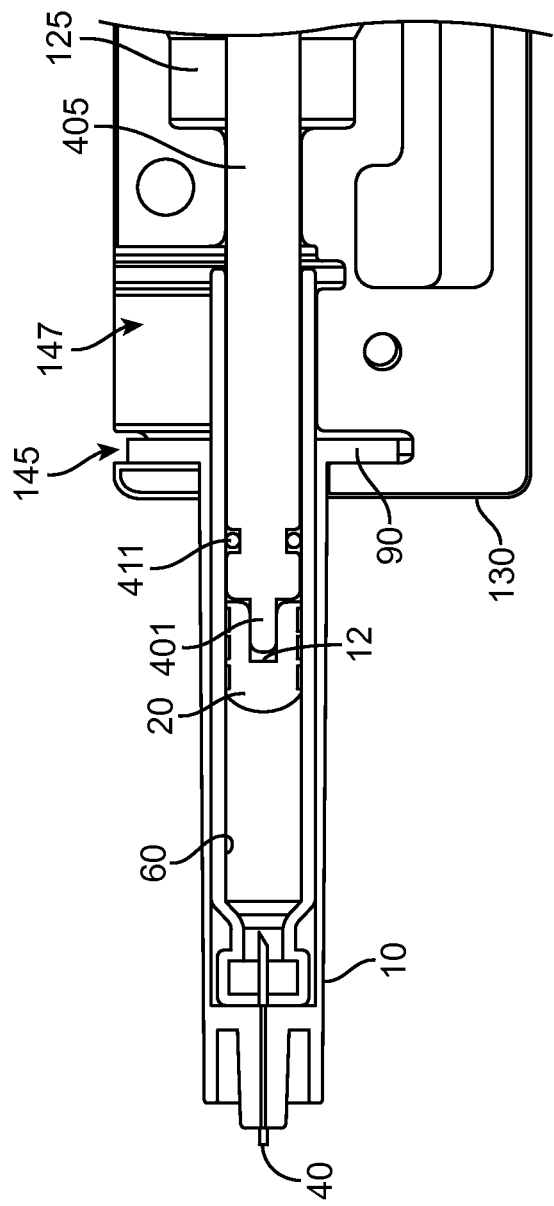
FIG. 6 shows a detailed cross-section of the injection device and the loaded container of FIG. 3.

FIG. 6 illustrates a detailed view of the plunger 405 pressing against the stopper 20 within the container 10. The distal end region 401 of the plunger 405 can extend into a proximal end of the container 10 to contact and engage the proximal side of the stopper 20. In one implementation, the distal end region 401 of the plunger 405 can have a projection that reversibly engages with a notch 12 located in a proximal side of the stopper 20. The notch 12 can have a shape corresponding to the shape of the projection. The plunger 405 can be urged distally such that it pushes against the stopper 20 and slides the stopper 20 through the barrel 60 towards the distal outlet 40. One or more sealing elements 411, such as O-rings or quad-rings, can be positioned around a portion of the plunger 405 to seal the components of the adjustment mechanism 110 from the material within the container 10 as well as a portion of the adjustment rod.

The injection device 100 also can include a trigger mechanism 120. As shown in FIGS. 4, 5, 8, 9, and 10 the trigger mechanism 120 can include a trigger handle 605, a front latch 615, a rear latch 620, and a release button 630 (shown in FIG. 1A). The front latch 615 can have a pivot point 615p constrained by the housing 115. The front latch 615 can also include an extension 617 that can sit within a notch 428 of the ribbed lower surface 427 of the advancing block 410. The rear latch 620 can have a pivot point 620p constrained by the rotating trigger handle 605 and an extension 627 that can sit within another notch 428 of the ribbed lower surface 427 of the advancing block 410. The front latch 615 and rear latch 620 can include torsion springs 624, 625 to urge the respective extensions 617, 627 into their respective notches 428 of the ribbed lower surface 427 of the advancing block 410. This can constrain the advancing block 410 from moving in a rearward or proximal direction while allowing for free movement of the advancing block 410 in a forward or distal direction.

The trigger handle 605 can be squeezed by a user such that it rotates relative to the housing 115 such as towards a pistol grip handle 117. It should be appreciated that the housing 115 can take on a variety of hand-held shapes and need not include a pistol grip handle 117. For example, the housing 115 can be configured to include a squeeze grip having the trigger mechanism 120 extending at an acute angle along the axis length of the housing 115. Any other number of configurations and designs can be used to orient the trigger mechanism 120 ergonomically or functionally along the housing 115.

As the trigger handle 605 rotates (arrow R in FIG. 9), the rear latch 620 can push against a notch 428 of the lower surface 427 of the advancing block 410 urging the advancing block 410 forward in the direction of arrow D along distance d. The pivot distances of the trigger handle 605 and the rear latch 620 provide a mechanical advantage that can allow a user to impart small forces at the trigger handle 605 that are translated into larger forces along the advancing block 410.

As the advancing block 410 advances distally along arrow D, the advancing block 410 applies a force to the proximal end of the advancing block spring 435 positioned within the bore 420 of the advancing block 410. The distal end of the advancing block spring 435, in turn, can press on the proximal end of the plunger 405 and cause it to move distally, such as further into the barrel 60 of the container 10 onto the stopper 20. The advancing block spring 435 can be, for example, a compressive spring element such as a compression spring as shown in the figures. The advancing block spring 435 can be constrained within the advancing block 410 such that it is maintained with an axial compressive load of a set threshold force. For example, the threshold force of the advancing block spring 435 can be between 5 and 75 lbf. In an exemplary embodiment, the threshold force can be 25 lbf. When the user activates the trigger handle 605 causing the advancing block 410 to move forward, a force is applied to the advancing block spring 435. The advancing block spring 435 in turn applies the force to the plunger 405. As the plunger 405 applies a force to the stopper of the container 10, the pressure of the material within the container 10 increases causing material to exit from the distal outlet 40. If the force required by the plunger 405 to cause the material to exit the outlet is less than the threshold force of the advancing spring block 435, then the advancing block spring 435 may not compress further and the movement of the advancing block 410 will be directly and linearly connected to the movement of the plunger 405 and therefore the rate of flow of the material through the distal outlet 40. This may be the case for materials that have a lower viscosity or if the container 10 is connected to a delivery instrument with a larger delivery lumen. However, if the force required by the plunger 405 to cause material to exit the distal outlet 40 is higher than the threshold force of the advancing block spring 435, then the advancing block spring element 435 may compress further. For example, if the threshold force is set a 25 lbf and the force required for material to flow through the distal outlet 40 of the container 10 at the rate of movement by the advancing block 410 reaches a peak force of 30 lbf, then the advancing block spring 435 may compress. The final distance moved by the advancing block 410 and the plunger 405 may be the same, but the time of the movement may be longer or the plunger 405. Therefore the flow rate of the material at the outlet and the peak pressure in the container 10 may be reduced.

As such, the user can be prevented from inducing a pressure on the container 10 that is higher than the force of the advancing block spring 435. This can be useful because pressures in the container 10 or applied to any component connected to the container 10 above a certain maximum force can cause a failure of those assemblies, which can be of particular importance when the mechanical advantage of a trigger mechanism 120 is so great that the user may not realize the excessive force is being applied. Additionally, the pressure and velocity of the material exiting the device in a tissue structure can be reduced. Therefore, the risk of damage to the tissue caused by pressures and velocities which are excessive can be potentially reduced.

In an alternative and interrelated implementation, the advancing block spring 435 can be a preloaded spring that has sufficient force to advance the plunger 405 distally. Instead of the trigger mechanism 120 exerting a force on the plunger 405 to push the plunger 405 forward as described above, the trigger mechanism 120 can meter the amount the plunger 405 is advanced by the preloaded advancing block spring 435.

Figure 10:
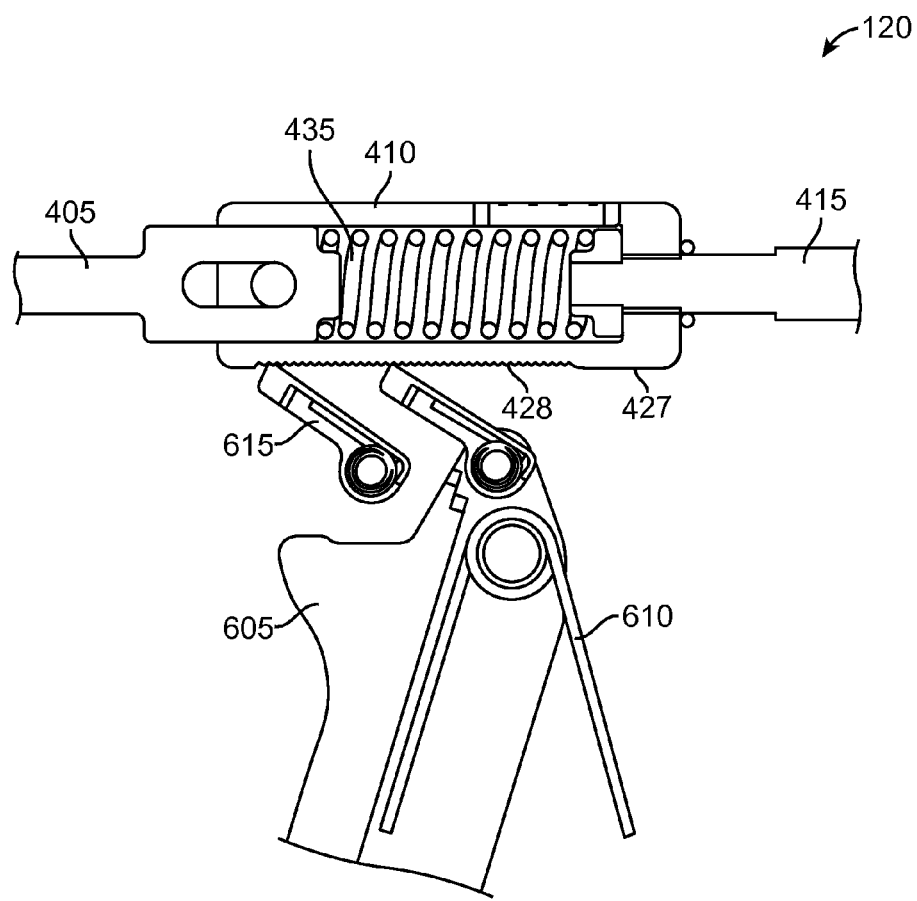

Now with respect to FIG. 10, once the trigger handle 605 is released by the user, a torsion spring 610 within the trigger handle 605 can return the trigger handle 605 to its start position and the front latch 615 can engage with the next notch 428 in the lower surface 427 of the advancing block 410. The advancing block spring 435 can return to its extended state. The front latch 615 can hold the mechanism stationary while the trigger handle 605 and rear latch 620 return to the start position allowing for step-wise advancement with trigger actuation. The user can repeat the process and squeeze the trigger handle 605 again to dispense another aliquot of material from the container 10. Each time the trigger handle 605 is squeezed, the advancing block 410 and plunger 405 can advance the distance d.

The metered volume of material delivered from a container 10 with each trigger handle 605 actuation can depend upon the travel distance d and the cross-sectional area of the container 10. Additionally, the travel distance d can vary along the axial length of the advancing block 410. The travel distance d can be the size of one advancing block notch 428 of the lower surface 427. In some implementations, the distance d can be between approximately 0.020" to approximately 0.060". In other implementations, the distance d can be 0.005" to approximately 0.120". The cross-sectional area of the container 10 can vary. The container 10 can have a cross-sectional area of 0.010 square inches to approximately 0.400 square inches.

For some containers, such as Healon 5, a distance d of approximately 0.036" of travel can correspond to approximately 60 uL of material dispensed from the container having cross-sectional area of approximately 0.050 square inches. It can be desirable to have an injector device 100 having alternate travel distances d depending on the cross-sectional area of the container intended to be used with the injector device 100. Other amounts or containers having other cross-sectional areas may have alternate distances d of the advancing block notches. For example, a first injection device 100 having a first distance d can be useful for the delivery of material from a first container having a first cross-sectional area according to a first metered dose of material. A second injection device 100 may have a second, larger distance d and can be useful for the delivery of material from a second container having a second, smaller cross-sectional area to deliver that same metered dose of material. In general, the equation V=A*d can be used to relate the distance d, the cross-sectional area A, and the volume displaced V.

The user can repeat the process and squeeze the trigger handle 605 again and again. Each time the trigger handle 605 is squeezed, the plunger 405 can advance the predetermined distance d. The lower surface 427 of the advancing block 410 can include notches 428 up to a predetermined point such that the plunger 405 is prevented from advancing beyond a certain overall distance into the container 10. For example, when the plunger 405 is close to the end of the container 10, it can be desirable for the plunger 405 to move no further in the distal direction.

Once the desired amount of material from the container 10 has been dispensed using the injection device 100, the user can release the container 10 from the injection device 100 by pressing the release button 630. The release button 630 can be located on the housing 115, for example along the side of the housing 115, extending through to pull the front latch 615 and the rear latch 620 away from the lower surface 427 of the advancing block 410 such that the advancing block 410 is clear to return in a rearward or proximal direction. The release button 630 can be connected to a cam shaft that translates the movement of the release button 630, which is perpendicular to the axial movement used to move the front latch 615 and the rear latch 620 away from the lower surface 427 of the advancing block 410, into an axial movement. A pin can be contained within a slot on the release button 630 and also contained by a hole on the cam shaft. As the release button 630 slides into the housing 115, the pin can be driven distally by the slot which, in turn, can pull the cam shaft distally and pull down the front latch 615 and the rear latch 620. A spring 418 can be positioned within bore 125 surrounding a portion of plunger 405 just distal to the proximal end region 407 (see FIGS. 5 and 7). The spring 418 can push the plunger 405, advancing block 410 and adjustment rod 415 in a proximal direction until the plunger 405 is withdrawn out from the barrel 60 of the container 10. Once the distal end 401 of the plunger 405 is clear of the container 10, the container 10 can be removed from the injection device 100, such as back up through the upper slot 147 of the fitted groove 145 region. The injection device 100 can be designed to be a single-use disposable device. Alternatively the injection device 100 can be a sterilizable device designed for reuse to deliver material from another container 10.

One or more components of the injection device 100, such as the trigger mechanism 120, can be formed of one or more biomedical compatible materials including, but not limited to biocompatible metals, anodized aluminum, stainless steel, or titanium. Alternatively, one or more components of the injection device 100 such as the trigger mechanism 120 can be formed of plastics such as polycarbonate, nylon, DELRIN or other suitable material. The components can be manufactured through machining processes such as milling or turning. Alternatively components can be manufactured through injection molding techniques or other suitable process. High strength components such as the advancing block 410, the front latch 615 and rear latch 620 can be formed of a metal material. Springs within the device such as the advancing block spring 435 and the spring 418 can be a plastic or metal material, including but not limited to stainless steel, music wire, a series of spring washers or other suitable material for delivering an appropriate force. In other embodiments the advancing block spring 435 or spring 418 can be a series of spring washers or a plastic plug capable of providing a spring force and spring rate. Forces delivered by one or both of the springs 435, 418 can be between about 10 lbf to about 40 lbf. Alternatively, forces delivered by one or both of the springs 435, 418 can be between about 5 lbf to about 75 lbf.

In other embodiments, the pushing mechanism for applying a force to the spring element may be any other variety of mechanisms such as a screw thread mechanism, a hydraulic mechanism, or any other suitable mechanism for advancing at predetermined distances.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An ophthalmic injection device, comprising:
a pistol-shaped housing having a grip handle and an elongated slot formed by straight edges formed on and extending through an outer side wall of the housing such that the slot is on an outer surface of the injection device:
a plunger mechanically coupled to the housing and configured to advance a distance into a container holding a material;
a pushing mechanism coupled to the housing and configured, upon an actuation of the pushing mechanism of a distance, to apply a force to a spring element, wherein the pushing mechanism comprises a trigger handle that pivots toward the grip handle when actuated; and
the spring element contained entirely within the housing and configured to apply the force to the plunger and configured to dampen the distance moved by the pushing mechanism from the distance moved by the plunger; and the container,
wherein the container is a cylindrical body that fits into the slot of the housing, wherein the container inserts into the slot on the outer side wall of the housing and wherein the container has a blunt distal end; and
a small delivery lumen configured to communicate with the container, wherein the small delivery lumen has an outlet configured to be placed within a structure of an eye.

2. The device in claim 1, wherein the spring element prevents the force applied to the plunger from reaching a threshold maximum.

3. The device in claim 1, wherein a metered volume of the material is delivered from the container with each actuation of the pushing mechanism.

4. The device in claim 3, wherein the metered volume is between 5 uL and 100 uL.

5. The device in claim 1, wherein the spring element is a compressive spring element.

6. The device in claim 5, wherein the compressive spring element is a compression spring.

7. The device in claim 5, wherein the compressive spring element has a spring rate of 30 lb/in to 150 lb/in.

8. The device in claim 5, wherein the compressive spring element is constrained axially in a state of compression such that the initial force to further compress the compressive spring element is a predetermined force.

9. The device in claim 8, wherein the initial force to further compress the compressive spring element is between 2 lbf and 50 lbf.

10. The device in claim 8, wherein the initial force to further compress the compressive spring element is adjustable.

11. The device in claim 1, wherein the container comprises a barrel, a stopper slideably disposed within the barrel, and an outlet.

12. The device in claim 11, wherein the plunger has a distal end that reversibly engages an end of the stopper.

13. The device in claim 12, wherein the plunger advances toward the outlet of the container and is configured to expel the material through the outlet.

14. The device in claim 11, wherein the outlet of the container communicates fluidly with a small delivery lumen.

15. The device in claim 14, wherein the small delivery lumen has an inner cross sectional area between $2.0E-4$ $in^2$ and $50E-4$ $in^2$.

16. The device in claim 1, wherein the structure of the eye is the suprachoroidal space.

17. The device in claim 1, wherein the structure of the eye is the Schlemm's Canal.

18. The device in claim 1, wherein the material in the container is a viscous substance.

19. The device in claim 18, wherein the viscous substance is a viscoelastic material used during ophthalmologic surgeries.

20. The device in claim 19, wherein the viscoelastic material is mixed with pharmaceutical agents.

21. The device in claim 1, wherein the pushing mechanism includes an advancing block which applies the force to the spring element.

22. The device in claim 21, wherein the pushing mechanism further includes a ratcheting mechanism wherein the advancing block may be moved by a predetermined distance upon activation of the pushing mechanism.

23. The device in claim 22, wherein the ratcheting mechanism includes at least one latch which engages with the advancing block and is configured such that the advancing block may not move in a proximal direction.

24. The device in claim 21, wherein the pushing mechanism includes a trigger which may engage with the advancing block to advance the advancing block by a predetermined distance when actuated.

25. The device in claim 24, wherein the predetermined distance is between 0.010 in and 0.075 in.

26. The device in claim 21, wherein the pushing mechanism includes a screw mechanism wherein the advancing block moves a predetermined distance upon a given rotation of the advancing block.

* * * * *